US 8,597,954 B2

(12) United States Patent
Tanigami et al.

(10) Patent No.: US 8,597,954 B2
(45) Date of Patent: Dec. 3, 2013

(54) STOOL SAMPLE PROCESSING METHOD AND STOOL SAMPLE PROCESSING CONTAINER

(75) Inventors: Yasuo Tanigami, Tokyo (JP); Kazue Nakajima, Tokyo (JP); Takami Shibazaki, Tokyo (JP)

(73) Assignee: Olympus Corporation, Tokyo (JP)

( * ) Notice: Subject to any disclaimer, the term of this patent is extended or adjusted under 35 U.S.C. 154(b) by 69 days.

(21) Appl. No.: 12/944,260

(22) Filed: Nov. 11, 2010

(65) Prior Publication Data

US 2011/0060137 A1    Mar. 10, 2011

Related U.S. Application Data

(63) Continuation of application No. PCT/JP2009/058622, filed on May 7, 2009.

(30) Foreign Application Priority Data

May 12, 2008   (JP) .................................. 2008-125143

(51) Int. Cl.
G01N 33/48    (2006.01)

(52) U.S. Cl.
USPC .................. 436/86; 436/89; 436/18; 436/175

(58) Field of Classification Search
USPC ....................................... 436/86, 89, 18, 175
See application file for complete search history.

(56) References Cited

U.S. PATENT DOCUMENTS

| | | | |
|---|---|---|---|
| 5,256,571 A | | 10/1993 | Hurley et al. |
| 5,998,483 A | * | 12/1999 | Camiener .................... 514/705 |
| 6,187,546 B1 | | 2/2001 | O'Neill et al. |
| 6,300,068 B1 | * | 10/2001 | Burg et al. .................... 435/6.14 |
| 6,916,608 B2 | * | 7/2005 | Berger et al. ................ 435/6.16 |
| 7,371,518 B2 | | 5/2008 | Lorincz et al. |
| 2001/0016317 A1 | | 8/2001 | Berger et al. |

(Continued)

FOREIGN PATENT DOCUMENTS

| | | |
|---|---|---|
| JP | 2668815 B2 | 10/1997 |
| JP | 11-511982 A | 10/1999 |

(Continued)

OTHER PUBLICATIONS

Lou et al. "Rapid and Effective Method for Preparation of Fecal Specimens for PCR Assays", Journal of Clinical Microbiology, Jan. 1997, p. 281-283.*

(Continued)

*Primary Examiner* — Monique Cole
(74) *Attorney, Agent, or Firm* — Westerman, Hattori, Daniels & Adrian, LLP

(57) ABSTRACT

The present invention relates to a stool sample processing method and stool sample processing container the a stool sample processing container provided with a stool collection tool, a suspending solution holding portion and a processing solution holding portion, wherein stool sample preparation solutions consisting of a suspending solution and a stool sample processing solution are respectively housed in a suspending solution holding container and a processing solution holding container, after first mixing a stool sample with the suspending solution and suspending therein, a sealant is released into the suspending solution holding container by pressing on the lower portion of the processing solution holding container, and the resulting stool suspension mixes with the stool sample processing solution that stabilizes the nuclide acid.

14 Claims, 6 Drawing Sheets

(56) References Cited

U.S. PATENT DOCUMENTS

| | | |
|---|---|---|
| 2002/0009722 A1 | 1/2002 | Berger et al. |
| 2003/0119049 A1 | 6/2003 | Lorincz et al. |
| 2006/0147944 A1 | 7/2006 | Chomczynski |
| 2006/0216714 A1 | 9/2006 | Kanaoka |
| 2008/0003564 A1 | 1/2008 | Chen et al. |

FOREIGN PATENT DOCUMENTS

| | | |
|---|---|---|
| JP | 2001-128661 A | 5/2001 |
| JP | 2001-128662 A | 5/2001 |
| JP | 2003-153688 A | 5/2003 |
| JP | 2004-500897 A | 1/2004 |
| JP | 2004-519202 A | 7/2004 |
| JP | 2005-532824 A | 11/2005 |
| WO | 97/09600 A2 | 3/1997 |
| WO | 00/08136 A1 | 2/2000 |
| WO | 00/63358 A1 | 10/2000 |
| WO | 01/98542 A2 | 12/2001 |
| WO | 2004/033622 A2 | 4/2004 |
| WO | 2004/083856 A1 | 9/2004 |
| WO | 2006/073497 A1 | 7/2006 |
| WO | 2007/100500 A2 | 9/2007 |
| WO | 00/63358 A1 | 11/2010 |

OTHER PUBLICATIONS

Lind, Guro et al. "A CpG island hypermethylation profile of primary colorectal carcinomas and colon cancer cell lines," Molecular Cancer, Oct. 2004, vol. 3, Chapter 28, pp. 1-11.

Nilsson, Hans-Olof, et al. "High Prevalence of *Helicobacter* Species Detected in Laboratory Mouse Strains by Multiplex PCR-Denaturing Gradient Gel Electrophoresis and Pyrosequencing," Journal of Clinical Microbiology, Aug. 2004, vol. 42, No. 8, pp. 3781-3788.

International Search Report of PCT/JP2009/058622, mailing date Jun. 30, 2009.

European Search Report dated Dec. 28, 2011, issued in corresponding European Patet Application No. 09746524.9.

Guillou J P et al., "Use of the in vitro enzymatic amplification method for the detection of *Mycobacterium paratuberculosis* in feces"; "2" In: Jun. 1993, Revue Scientifique Et Technique (International Office of Epizootics) Jun. 1993 LNKD—PUBMED:8400396, vol. 12, pp. 605-615.

Lantz Par-Gunnar et al., "Removal of PCR inhibitors from human faecal samples through the use of an aqueous two-phase system for sample preparation prior to PCR", Journal of Microbiological Methods, Elsevier, Amsterdam, NL, vol. 28, No. 3, Jan. 1, 1997, pp. 159-167.

* cited by examiner

STOOL SAMPLE PROCESSING METHOD AND STOOL SAMPLE PROCESSING CONTAINER

TECHNICAL FIELD

The present invention relates to a stool sample processing method and stool sample processing container for efficiently recovering nucleic acids from stool samples.

The present application claims priority on the basis of Japanese Patent Application No. 2008-125143, filed in Japan on May 12, 2008, the contents of which are incorporated herein by reference.

BACKGROUND ART

The number of colorectal cancer patients is currently continuing to increase rapidly each year in not only the U.S. and Europe, but in Japan as well, and is becoming one of the leading causes of cancer-related deaths. In Japan, this is thought to be due to the growing proliferation of a Western style diet consisting primarily of red meat among the Japanese people. More specifically, roughly 60,000 persons are diagnosed with colorectal cancer each year in Japan. In terms of the number of deaths by organ, colorectal cancer is ranked third after gastric cancer and lung cancer, and is predicted to continue to increase in the future. On the other hand, differing from other forms of cancer, colorectal cancer has a nearly 100% cure rate if treated soon after onset. Thus, it is of the utmost importance to include colorectal cancer in early cancer screening examinations, and in consideration thereof, research and development of testing methods for early discovery of colorectal cancer is proceeding at a rapid pace.

Methods such as barium enema examinations and colonoscopies are performed as testing methods for early discovery of colorectal cancer. Barium enema examinations consist of injecting barium into the large intestine and allowing it to adhere to the mucosal membranes of the large intestine, irradiating the intestine with X-rays to capture images of any surface irregularities, and then observing the surface. On the other hand, colonoscopy consists of observing the inside of the large intestine directly with an endoscope. Colonoscopy in particular enables high levels of sensitivity and specificity, while also offering the advantage of simultaneously allowing the excision of polyps and early forms of cancer.

However, in addition to be associated with high costs, these examinations place a considerable burden on the patient while also having the problem of being accompanied by complication risks. For example, barium enemas have risks associated with X-ray exposure and intestinal obstruction. In addition, colonoscopy is an invasive procedure for the subject since the endoscope is inserted directly into the large intestine. Moreover, the endoscopic procedures requires an experienced technician and the number of facilities were this examination can be performed is limited. Consequently, these examinations are not suitable for colorectal cancer examinations targeted at asymptomatic, healthy individuals as part of routine health examinations and the like.

In recent years, fecal occult blood tests have been widely performed as a non-invasive and inexpensive method for primary screening for colorectal cancer. The fecal occult blood test is a test for the presence of hemoglobin originating in erythrocytes contained in fecal matter, and is used as a method for indirectly predicting the presence of colorectal cancer. Factors behind the widespread use of the fecal occult blood test include stool samples being able to be collected and stored at room temperature eliminating the need for refrigerators, freezers and other special storage conditions, samples being able to be collected easily at home, and the test procedure being extremely simple. However, since the fecal occult blood test has low sensitivity of only about 25%, it has the problem of a high percentage of colorectal cancer being overlooked. Moreover, it also has a low positive predictive value, with the percentage of actual colorectal cancer patients among subjects judged to be positive in the fecal occult blood test being only 10% or less, thus resulting in a large number of false positives. Consequently, there is a strong need for the development of a new examination method offering higher reliability.

Attention is currently focusing on new examination methods that are suitable for routine health examinations by being non-invasive, simple and highly reliable for use in testing for the presence of cancer cells and cancer cell-derived genes in stool samples. Since these examination methods investigate the presence of cancer cells or cancer cell-derived genes directly, they are considered to be more reliable than the fecal occult blood test, which tests for the presence of blood from the digestive tract that occurs indirectly accompanying the onset of colorectal cancer.

In order to accurately detect cancer cells and the like in stool samples, it is important to efficiently recover cancer cell-derived nucleic acids from those stool samples. In particular, cancer cell-derived nucleic acids are only present in trace amounts in stool samples, and since stool samples also contain large amounts of digestive remnants and bacteria, nucleic acids are decomposed extremely easily. Consequently, in order to efficiently recover nucleic acids, and particularly nucleic acids derived from mammalian cells such as human cells, from stool samples, it is important to prevent decomposition of nucleic acids within the stool and prepare the stool sample so that it can be stored stably until the time of the actual testing procedure. An example of such a stool sample processing method consists of separating cancer cells that have dissociated from the large intestine or other constituent of the digestive tract from a collected stool sample. Separation of cancer cells from stool makes it possible to inhibit the effects of bacterial proteases, DNase, RNase and other degrading enzymes. An example of a method that has been disclosed for separating cells from stool consists of cooling the stool sample to a temperature below its gel freezing point, and collecting cells while maintaining at a temperature below the gel freezing point so that the stool substantially remains completely intact (see, for example, Patent Document 1). In addition, another method that has been disclosed consists of dispersing the stool sample in a transport medium containing a protease inhibitor, mucous dissolver and bactericide at a normal ambient temperature, followed by isolating the colorectal dissociated cells (see, for example, Patent Document 2).

On the other hand, numerous fixation methods, such as formalin fixation or alcohol fixation, have conventionally been employed to maintain the morphology of collected cells until the time of observation for the purpose histological and cytological observation of cell morphology. An example of a method that employs these fixation methods consists of a sample processing method that uses the following special cell solution preservative to enable mammalian cell samples to be stored for long periods of time or enable cells to be observed following storage (see, for example, Patent Document 3). This cell solution preservative includes an amount of water sufficient for colonizing mammalian cells, a miscible alcohol, an amount of anti-aggregation agent sufficient for preventing aggregation of mammalian cells in the solution, and a buffer for maintaining the pH of the solution within the range of 4 to 7 during the time the cells are stored.

In addition, a sample processing method that uses the storage solution described below is an example of a method that uses a storage solution allowing molecular analysis of proteins and nucleic acids present in cells following storage in addition to cell histological and cytological observations. Patent Document 4 discloses a sample processing method that uses a universal collection medium containing a buffer component, at least one alcohol component, a fixative component and at least one chemical agent that inhibits decomposition of at least one substance selected from the group consisting of RNA, DNA and protein, while Patent Document 5 discloses a sample processing method that uses a non-aqueous solution containing 5 to 20% polyethylene glycol and 80 to 95% methanol.

In addition, Patent Document 6 discloses a sample processing solution containing alcohol or ketone for stabilizing cells present in vaginal swabs and viral nucleic acids, and further containing a substance for precipitating or denaturing proteins along with a promoter for promoting injection into cells.

In addition, Patent Document 7 discloses a stool sample processing container that suspends an extremely small amount of collected stool sample on the order of about 0.03 g by mixing with a suspension containing a storage solution and the like for the purpose of fecal occult blood testing.

PRIOR ART DOCUMENTS

[Patent Documents]
[Patent Document 1] Published Japanese Translation of PCT Application No. H11-511982
[Patent Document 2] Published Japanese Translation of PCT Application No. 2004-519202
[Patent Document 3] Japanese Unexamined Patent Publication No. 2003-153688
[Patent Document 4] Published Japanese Translation of PCT Application No. 2004-500897
[Patent Document 5] Published Japanese Translation of PCT Application No. 2005-532824
[Patent Document 6] Japanese Unexamined Patent Publication No. 2001-128662
[Patent Document 7] Japanese Patent No. 2668815

SUMMARY OF THE INVENTION

Problems to be Solved by the Invention

However, in a stool sample processing method in which the stool sample is processed while maintaining at a low temperature in the manner of the aforementioned Patent Document 1, it is necessary to cool the stool sample immediately after collection. Therefore, in the case of collecting a stool sample at home as is done in the case of routine health examinations, it is extremely difficult to promptly cool the stool sample after collection. In addition, although it is possible to freeze the stool sample to prevent deterioration, a frozen stool sample must be thawed prior to testing. Frozen stool samples are usually crushed prior to thawing since it is preferable to perform the thawing procedure in a short period of time to prevent degradation and so forth of nucleic acids in the stool sample as much as possible.

However, frozen stool samples are difficult to crush and difficult to handle due to their high hardness. In addition, there is the risk of contamination and infection due to dispersal of frozen pieces during crushing. In addition, in the stool sample processing method indicated in Patent Document 2 consisting of the addition of a bactericide and the like, although this method does not require a cooling procedure and allows preparation and storage of stool samples at room temperature, the procedure for separating cells that have dissociated from the large intestine from stool is complex. Moreover, exfoliated colonocytes and nucleic acids and the like derived from the exfoliated colonocytes end up being decomposed by nucleases and proteases derived from bacteria destroyed by the bactericide and the like. As a result, there is the risk of a decrease in the detection accuracy of colorectal cancer. In addition, there is also the problem of gene expression and other molecular profiling of the exfoliated colonocytes having an effect on antibiotics and other components in the medium as well as causing cells within the stool sample to be altered by deterioration and decomposition over the passage of time.

In addition, although the stool sample processing methods using each of the storage solutions indicated in the aforementioned Patent Documents 3 to 5 enable cells to store stably at room temperature, these storage solutions are used for isolated cells that are free of impurities such as tissue and other cells, and encounter difficulties when used directly for biological samples such as stool samples containing various substances. In the case of using these storage solutions for exfoliated colonocytess present in stool samples, since the exfoliated colonocytes are only present in trace amounts therein, it is difficult to extract an amount of nucleic acid from the isolated cells that is sufficient for analysis. In addition, the sample processing solution indicated in Patent Document 6 is used to stably store nucleic acids primarily derived from bacteria present in vaginal swab samples. Stool samples, however, are in the form of a mixture of a large amount of bacteria, a large amount of digestive remnants and extremely small amounts of nucleic acids derived from mammalian cells. There is no mention whatsoever in Patent Document 6 of a sample storage solution capable of also stably storing nucleic acids derived from mammalian cells that are present in much smaller amounts than bacteria.

Moreover, in the stool sample processing container used to perform fecal occult blood tests indicated in Patent Document 7, the amount of stool sample that can be processed is extremely low at only about 0.03 g and substantially only one type of stool sample processing solution can be housed in the container. Consequently, in the case of recovering nucleic acids from stool samples using this storage solution, it is necessary to add the storage solution to a suspension, thereby causing the suspension efficiency to be lowered by the action of the storage solution in the suspension and resulting in a corresponding decrease in nucleic acid recovery efficiency, thereby preventing nucleic acids from being recovered with high accuracy.

With the foregoing in view, an object of the present invention is to provide a stool sample processing method and a stool sample processing container that enable nucleic acids to be recovered with high accuracy.

Means for Solving the Problems

The present invention employs the following means to solve the aforementioned problems and achieve the object of the present invention.
(1) A stool sample processing method for preparing and processing a stool sample for recovering a nucleic acid from collected stool samples, including: a suspension step for forming a stool suspension in which the collected stool sample is suspended with a suspending solution, and a sample preparation step for preparing the stool sample by mixing the stool suspension with a stool sample processing solution that stabilizes the nucleic acid.

(2) The suspending solution used in the stool sample processing method described in (1) above is preferably selected from the group consisting of water, physiological saline or a buffer.

(3) The stool sample processing solution used in the stool sample processing method described in (1) or (2) above is preferably a water-soluble organic solvent.

(4) The water-soluble organic solvent used in the stool sample processing method described in (3) above is preferably a water-soluble alcohol and/or ketone.

(5) The stool sample used in the stool sample processing method described in (3) or (4) above preferably contains 30% or more of the water-soluble organic solvent.

(6) The water-soluble alcohol used in the stool sample processing method described in (4) above is preferably one or more types selected from the group consisting of ethanol, propanol and methanol.

(7) The ketone used in the stool sample processing method described in (4) above is preferably acetone and/or methyl ethyl ketone.

(8) The water-soluble organic solvent used in the stool sample processing method described in (3) above is preferably an aldehyde.

(9) The stool sample used in the stool sample processing method described in (3) or (8) above preferably contains 0.01 to 30% of the water-soluble organic solvent.

(10) The suspending solution and/or stool sample processing solution used in the stool sample processing method described in any of (1) to (9) above preferably contains a surfactant.

(11) The suspending solution and/or stool sample processing solution used in the stool sample processing method described in any of (1) to (10) preferably contains a colorant.

(12) The water-soluble organic solvent used in the stool sample processing method described in any of (3) to (9) above preferably contains an organic acid.

(13) The water-soluble organic solvent used in the stool sample processing method described in any of (3) to (9) above preferably contains a chelating agent and/or polycation.

(14) The present invention also provides a stool sample processing container for preparing and processing stool samples for recovering nucleic acids from collected stool samples, provided with: a suspending solution holding portion that holds a suspending solution for suspending a stool sample, an introduction mechanism that introduces the stool sample into the suspending solution holding portion, a processing solution holding portion that holds a stool sample processing solution that stabilizes the nucleic acids, and a release mechanism that releases an opening between the suspending solution holding portion and the processing solution holding portion.

(15) The release mechanism provided in the stool sample processing container described in (14) above is preferably provided with a communicating hole that connects the suspending solution holding portion and the processing solution holding portion, and a sealing portion provided in the communication hole that seals communication; wherein, the processing solution holding portion is preferably a flexible container, and the stool sample processing solution is preferably allowed to flow toward the suspending solution by cancelling sealing of the sealing portion by increasing pressure of the processing solution by contracting the processing solution holding container.

(16) The processing solution holding portion provided in the stool sample processing container described in (14) or (15) above is preferably flexible in the axial direction, and preferably allows all of the stool sample processing solution to flow toward the suspending solution holding portion.

(17) The release mechanism provided in the stool sample processing container described in (14) above is preferably provided with a sealing portion that seals an opening between the suspending solution holding portion and the processing solution holding portion, and a protruding portion that releases the opening between the suspending solution holding portion and the processing solution holding portion by puncturing the sealing portion.

(18) The release mechanism provided in the stool sample processing container described in (14) above is preferably provided with a sealing portion that seals an opening between the suspending solution holding portion and the processing solution holding portion, and a protruding portion that releases the opening between the suspending solution holding portion and the processing solution holding portion by pressing on the sealing portion.

(19) The processing solution holding portion provided in the stool sample processing container described in (14) above is preferably formed within the suspending solution holding portion, the suspending solution holding portion and the processing solution holding portion are preferably formed with elastic materials, and the stool sample processing solution is preferably allowed to flow toward the suspending solution by rupturing the processing solution holding portion by pressing from outside the suspending solution holding portion and the processing solution holding portion.

(20) The processing solution holding portion provided in the stool sample processing container described in (14) above is preferably formed within the suspending solution holding portion, the suspending solution holding portion and the processing solution holding portion are preferably formed with elastic materials, the tensile strength of a portion of the processing solution holding portion is preferably lower than the tensile strength of the suspending solution holding portion, and the stool sample processing solution is preferably allowed to flow toward the suspending solution by rupturing the portion of weak tensile strength of the processing solution holding portion by bending the suspending solution holding portion and the processing solution holding portion from outside the suspending solution holding portion and the processing solution holding portion.

(21) In the stool sample processing container described in (14) above, at least the suspending solution holding portion and the processing solution holding portion are preferably separate portions, and the suspending solution holding portion and the processing solution holding portion are preferably mutually attachable.

(22) The suspending solution used in the stool sample processing container described in (14) above is preferably selected from the group consisting of water, physiological saline or buffer.

(23) The stool sample processing solution used in the stool sample processing container described in (14) or (22) above is preferably a water-soluble organic solvent.

(24) The water-soluble organic solvent used in the stool sample processing container described in (23) above is preferably a water-soluble alcohol and/or ketone.

(25) The stool sample used in the stool sample processing container described in (23) or (24) above preferably contains 30% or more of the water-soluble organic solvent.

(26) The water-soluble alcohol used in the stool sample processing container described in (24) above is preferably one or more types selected from the group consisting of ethanol, propanol and methanol.

(27) The ketone used in the stool sample processing container described in (24) above is preferably acetone and/or methyl ethyl ketone.
(28) The water-soluble organic solvent used in the stool sample processing container described in (23) above is preferably an aldehyde.
(29) The stool sample used in the stool sample processing container described in (23) or (28) above preferably contains 0.01 to 30% of the water-soluble organic solvent.
(30) The suspending solution and/or stool sample processing solution used in the stool sample processing container described in any of (14) or (22) to (29) above preferably contains a surfactant.
(31) The suspending solution and/or stool sample processing solution used in the stool sample processing container described in any of (14) or (22) to (30) above preferably contains a colorant.
(32) The water-soluble organic solvent used in the stool sample processing container described in any of (23) to (29) above preferably contains an organic acid.
(33) The water-soluble organic solvent used in the stool sample processing container described in any of (23) to (29) above preferably contains a chelating agent and/or polycation.

Effects of the Invention

According to the present invention, since a stool sample processing solution is mixed after mixing a stool sample with a suspending solution and suspending therein, nucleic acid recovery efficiency and recovery accuracy can be improved as a result of improving suspension efficiency.

BEST MODE FOR CARRYING OUT THE INVENTION

Figure 1:
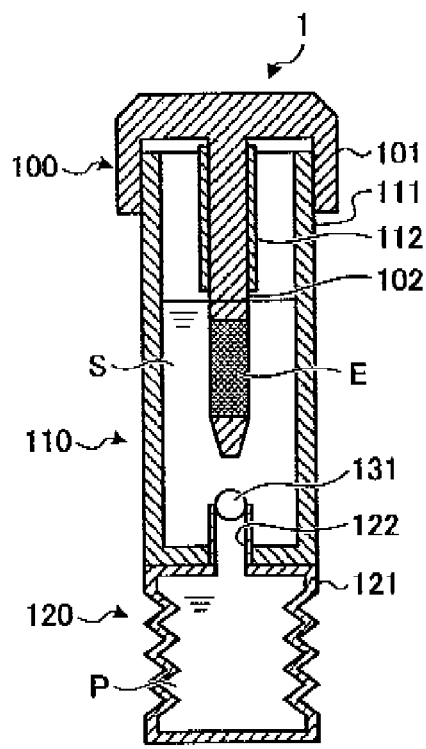
FIG. 1 is a schematic drawing showing a stool sample processing container 1 relating to a first embodiment.

The following provides an explanation of a stool sample processing method and stool sample processing container, which are embodiments of the present invention, with reference to the drawings. Furthermore, the present invention is not limited by these embodiments. In addition, the same reference symbols are used to indicate the same constituents in the drawings.

First Embodiment

FIG. 1 is a schematic drawing showing the general configuration of a stool sample processing container 1 relating to a first embodiment of the present invention. This stool sample processing container 1 is provided with a stool collection tool 100, a suspending solution holding portion 110, and a processing solution holding portion 120. These members are each present within the stool sample processing container 1 in a sealed state, and are each removable. In addition, a suspending solution S and a stool sample processing solution P that compose a stool sample preparation solution are housed in the suspending solution holding container 111 and a processing solution holding container 121, respectively.

In the stool sample processing container shown in FIG. 1, the height of the level of the suspending solution S housed in the suspending solution holding container 111 is preferably higher than a stool sample E collected in a stool collection rod 102. In addition, a valve and the like may also be provided for preventing leakage of liquid corresponding to the height of the level of the suspending solution S. In addition, a slider 112 is installed in the suspending solution holding container 111, and in the case of attaching a cover 101 to the suspending solution holding container 111, the amount of the stool sample E can be made to be constant by scraping off excess stool adhered to the stool collection rod 102 with the slider 112. Furthermore, in the present embodiment, the cover 101 and the stool collection rod 102, by which the stool sample E is introduced into the suspending solution holding container 111, are referred to as an introduction mechanism. After having collected the stool sample E with the stool collection rod 102, the cover 101 is connected to the suspending solution holding container 111 and a stool sample suspension is formed as a result of a fixed amount of the collected stool sample E being mixed and suspended in the suspending solution S.

Figure 2:
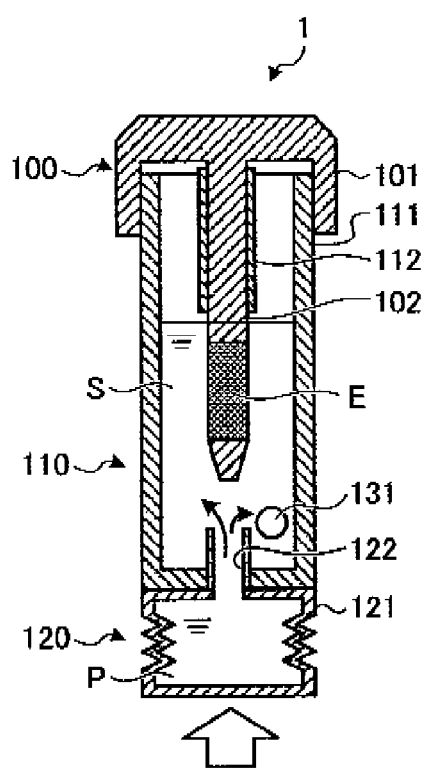
FIG. 2 is a schematic drawing showing a stool sample processing container 1 relating to a first embodiment.

Next, the stool sample suspension suspended in the suspending solution holding container 111 is mixed with the stool sample processing solution P. As shown in FIG. 2, the volume inside the processing solution holding container 121 is reduced and the internal pressure of the processing solution holding container 121 is increased by pressing on the lower portion of the processing solution holding container 121. At this time, a sealant 131 is released into the suspending solution holding container 111 from a sealant shaft portion 122 resulting in mixing of the stool sample suspension and the stool sample processing solution P. Furthermore, in the present embodiment, the sealing 131 and the sealant shaft portion 122 constitute a release mechanism. This mixture serves as a stool sample for recovering amino acids from fecal matter. Furthermore, the processing solution holding container 121 is preferably formed from a material such as aluminum foil or other metal foil, rubber or plastic. In addition, the lower portion of the processing solution holding container 121 can be contracted to the upper portion of the processing solution holding container 121, enabling all the stool sample processing solution to flow towards the suspending solution holding container 111. Moreover, by repeatedly stretching and contracting the processing solution holding container 121, the stool sample suspension can be efficiently mixed with the stool sample processing solution P.

Although there are no particular limitations thereon, examples of the suspending solution S used in the stool sample processing method of the present invention include physiological saline, water, 2-morpholinoethane sulfonic acid (MES) buffer, bis(2-hydroxethyl)iminotris(hydroxymethyl) methane (Bis-Tris) buffer, tris(hydroxymethyl)aminomethane (Tris) buffer, N-(2-acetoamido)iminodiacetic acid (ADA) buffer, piperazine-N,N'-bis(2-ethanesulfonic acid) (PIPES) buffer, 2-[N-(2-acetoimido)amino]ethanesulfonic acid (ACES) buffer, 3-morpholino-2-hydroxypropanesulfonic acid (MOPSO) buffer, 2-[N,N-bis(2-hydroxyethyl)amino]ethanesulfonic acid (BES) buffer, 3-morpholinopropanesulfonic acid (MOPS) buffer, 2-{N-[tris(hydroxymethyl)methyl]amino}ethanesulfonic acid (TES) buffer, N-(2-hydroxyethyl)-N'-(2-sulfoethyl)piperazine (HEPES) buffer, 3-[N,N-bis(2-hydroxyethyl)amino]-2-hydroxypropanesulfonic acid (DIPSO) buffer, 2-hydroxy-3-{[N-tris(hydroxymethyl)methyl]amino}propanesulfonic acid (TAPSO) buffer, piperazine-N,N'-bis(2-hydroxypropane-3-sulfonic acid) (POPSO) buffer, N-(2-hydroxyethyl)-N'-(2-hydroxy-3-sulfopropyl)piperazine (HEPPSO) buffer, N-(2-hydroxyethyl)-N'-(3-sulfopropyl)piperazine (EPPS) buffer, tricine[N-tris(hydroxymethyl)methylglycine] buffer, bicine[N,N-bis(2-hydroxyethyl)glycine] buffer, 3-[N-tris (hydroxymethyl)methyl]aminopropanesulfonic acid (TAPS) buffer, 2-(N-cyclohexylamino)ethanesulfonic acid (CHES) buffer, 3-(N-cyclohexylamino)-2-hydroxypropanesulfonic acid (CAPSO) buffer, and 3-(N-cyclohexylamino)propanesulfonic acid (CAPS) buffer.

In addition, the stool sample processing solution P contains a water-soluble organic solvent having an action that stabilizes nucleic acids. Although there are no particular limitations on the water-soluble organic solvent contained in the stool sample processing solution P provided it is a compound that is able to demonstrate a nucleic acid stabilizing effect, caution is required so that the nucleic acid stabilizing effect is not impaired as a result of reacting with the stool suspension. Examples of water-soluble organic solvents include alcohols, ketones and aldehydes. Examples of ketones include acetone and methyl ethyl ketone, and examples of aldehydes include acetoaldehyde (acetylaldehyde), formaldehyde (formalin), glutaraldehyde, paraformaldehyde and glyoxal. The water-soluble organic solvent used in the present invention is preferably a water-soluble alcohol, acetone or methyl ethyl ketone, and more preferably a water-soluble alcohol. In addition, ethanol, propanol or methanol is even more preferable from the viewpoints of availability, handling ease, safety and the like. Propanol may be n-propanol or 2-propanol. Since ethanol in particular has the highest degree of safety and is readily available even in the home, it is particularly useful for routine health examinations and other screening tests.

Furthermore, as a result of conducting further studies, the inventors of the present invention found that nucleic acids derived from mammalian cells such as exfoliated colonocytes present in stool samples can be recovered efficiently. The method used to process such stool samples consists of mixing the collected stool sample in a stool sample preparation solution having a water-soluble organic solvent as an active ingredient thereof, and simultaneously recovering nucleic acids derived from indigenous intestinal flora and nucleic acids derived from a biological origin other than indigenous intestinal flora from the stool sample consisting of a mixture of the stool sample and the stool sample preparation solution.

Since the concentration of water-soluble organic solvent in the stool sample processing solution P is desired to be an effective concentration of the water-soluble organic solvent after mixing with the stool suspension, it is necessary to arbitrarily set the volume and concentration so as to reach an optimal final concentration. There are no particular limitations on the final concentration of the water-soluble organic solvent in the mixture after mixing the stool suspension and the stool sample processing solution P provided it is a concentration that allows the demonstration of the nucleic acid stabilizing effect, and can be suitably determined in consideration of the type of water-soluble organic solvent and the like. For example, in the case of using a water-soluble alcohol or ketone as an active ingredient, the concentration of the water-soluble organic solvent in the mixture after mixing the stool suspension and the stool sample processing solution P is preferably 30% or more. In the case of having mixed the stool suspension and the stool sample processing solution P, as the concentration of the water-soluble organic solvent becomes higher, the components of the water-soluble organic solvent permeate more rapidly into the mammalian cells and indigenous intestinal flora present in the stool sample, thereby making it possible to rapidly stabilize nucleic acids.

In the case of using a water-soluble alcohol for the active ingredient in particular, the concentration of the water-soluble alcohol in the stool sample in which the stool suspension is mixed with the stool sample processing solution P is preferably 30% or more, more preferably 50% or more, even more preferably 50 to 80%, and particularly preferably 60 to 70%. The higher the concentration of the water-soluble organic solvent, an effect sufficient for stabilizing nucleic acids can be obtained using a smaller amount of stool sample preparation solution even for stool samples having a high water content.

In addition, in the case of using acetone or methyl ethyl ketone for the active ingredient, the concentration of acetone or methyl ethyl ketone in the stool sample is preferably 30% or more, more preferably 60% or more, and even more preferably 80% or more. In the case of using acetoaldehyde, formaldehyde, glutaraldehyde, paraformaldehyde or glyoxal for the active ingredient, the concentration of these active ingredients in the stool sample is preferably within the range of 0.01 to 30%, more preferably within the range of 0.03 to 10%, and even more preferably within the range of 3 to 5%.

Furthermore, the water-soluble organic solvent used in the stool sample processing solution P may contain only one type of water-soluble organic solvent or may be mixed solution of two or more types of water-soluble organic solvents. For example, the water-soluble organic solvent may be a mixture of two or more types of alcohols or a mixed solution of an alcohol and other types of water-soluble organic solvents. A mixed solution of alcohol and acetone is preferable for further improving nucleic acid recovery efficiency.

Furthermore, although there are no particular limitations on the stool used in the stool sample processing method of the present invention provided it is of animal origin, that of mammalian origin is preferable while that of human origin is more preferable. For example, although human stool collected for the purpose of routine health examinations, diagnosis and so forth is preferable, stool of livestock or wild animals and the like may also be used. In addition, although stool that has been stored for a fixed period of time after collection may be used, it is preferably used immediately after collection. Moreover, although the collected stool is preferably obtained immediately after voiding, that for which time has elapsed after voiding may also be used.

In addition, although there are no particular limitations on the amount of the stool sample, it is preferably within the range of 0.05 to 1 g. Moreover, the amount of the stool sample is particularly preferably within the range of 0.1 to 1 g in order to enhance the effectiveness of nucleic acid recovery. If the amount of the stool sample is excessively large, the collection procedure becomes difficult and the size of the collection container also increases, thereby resulting in the risk of a decrease in handling ease and the like. Conversely, in the case the amount of the stool sample is excessively small, since the number of exfoliated colonocytes and other mammalian cells contained in the stool become excessively low, the necessary amount of nucleic acid cannot be recovered, thereby resulting in the risk of a decrease in the target accuracy of nucleic acid analysis. In addition, since stool is inherently heterogeneous, or in other words, numerous types and forms of components are non-uniformly present therein, the stool sample is preferably collected from a wide range of the stool at the time of stool collection to avoid the effect of localization of mammalian cells.

In addition, the suspending solution S and the stool sample processing solution P may also contain a surfactant. The surfactant contained in the stool sample preparation solution is preferably a nonionic surfactant. Examples of nonionic surfactants include Tween 80, CHAPS (3-[3-cholamidopropyldimethylammonio]-1-propanesulfonate, Triton X-100 and Tween 20. There are no particular limitations on the types or concentrations of chaotropic salts or surfactants provided their concentrations allow the obtaining of a nucleic acid stabilizing effect, and can be suitably determined in consideration of such factors as the amount of stool and the methods used for subsequent nucleic acid recovery and analysis.

In addition, a suitable colorant may be added to the suspending solution S and the stool sample processing solution P. Coloring the suspending solution S and the stool sample processing solution P allows obtaining of effects such as prevention of accidental swallowing and reducing stool color. The colorant is preferably a colorant used as a food additive, and is preferably blue or green and the like. Examples of colorants include Fast Green FCF (Green No. 3), Brilliant Blue FCF (Blue No. 1) and Indigo Carmine (Blue No. 2). In addition, a plurality of colorants may be used as a mixture or a single colorant may be added alone.

In addition, the suspending solution S and the stool sample processing solution P may also contain an organic acid. The addition of an organic acid minimizes loss of nucleic acids contained in stool due to decomposition and the like, thereby making it possible to improve the stability of nucleic acids in the water-soluble organic solvent. Examples of organic acids include linear aliphatic acids, dicarboxylic acids, amino acids, hydroxy acids, aromatic or heterocyclic polycarboxylic acids, acetic acid, adipic acid, citric acid and lactic acid.

In particular, linear aliphatic acids, dicarboxylic acids and hydroxy acids are preferable, while acetic acid, adipic acid, citric acid and lactic acid are more preferable. The use of adipic acid or citric acid makes it possible to obtain particularly superior nucleic acid preservation effects. In addition, acetic acid is preferable since in addition to allowing the obtaining of adequate nucleic acid preservation effects, is also widely used and economical.

Furthermore, the suspending solution S and the stool sample processing solution P may contain only one type of organic acid or may contain two or more types of organic acids. In addition, there are no particular limitations on the amount of organic acid added to the stool sample preparation solution of the present invention provided it is an amount that is capable of maintaining acidity, and can be suitably determined in consideration of such factors as the type of organic acid added, and the type and concentration of the water-soluble organic solvent present in the stool sample processing solution.

In addition, the suspending solution S and the stool sample processing solution P may also contain a chelating agent and/or polycation. The addition of a chelating agent and/or polycation makes it possible to recover nucleic acids from the stool sample with high purity by removing substances that inhibit nucleic acid analysis contained in the stool sample.

A chelating agent refers to a ligand that forms a chelate complex. Examples of chelating agents include ethylenediamine tetraacetate (EDTA), glycine (Bicine) and ethylene glycol tetraacetate (EGTA). Furthermore, the stool sample preparation solution of the present invention may contain only one type of chelating agent or may contain two or more types of chelating agents.

There are no particular limitations on the concentration of the added chelating agent provided it is a concentration that is sufficient for removing inhibitory substances in the stool sample, and can be suitably determined in consideration of such factors as the type of chelating agent. Each chelating agent is added so that the final concentration of chelating agent in the stool sample preparation solution of the present invention is preferably within the range of 0.1 to 1 M.

In addition, a polycation refers to a polymer compound or salt thereof that has a repeating structure containing a cationic functional group. An example of a cation is an amino group. More specifically, polylysine or polyacrylamide is preferable, and polylysine is more preferable. Other examples include polypeptides having cationic functional groups in a side chain such as polylysine indicated in the following formula (1), and polymers obtained by polymerizing a monomer containing cationic functional groups such as polyacrylamide. Furthermore, these polypeptides and polymers are only required to be electrically positive overall, and although they are not required to have cationic functional groups in the side chains of all repeating units (amino acids or monomers), they preferably have cationic functional groups in the side chains of all repeating units. Furthermore, the stool sample preparation solution of the present invention may contain only one type of polycation or may contain two or more types of polycations.

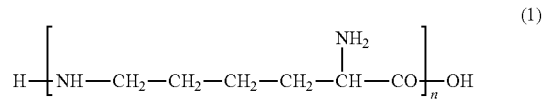

(1)

There are no particular limitations on the concentration of polycation added to the suspending solution S and the stool sample processing solution P provided it is a concentration sufficient for obtaining the effect of reducing inhibitory action of inhibitory substances contained in a nucleic acid-containing stool sample (inhibitory action reduction effect), and can be suitably determined in consideration of such factors as the type of polycation, the type of nucleic acid-containing stool sample, the pH of the stool sample preparation solution, and the mixing ratio of the stool sample preparation solution and the nucleic acid-containing stool sample. For example, in the case of containing polylysine for the polycation, the concentration of polylysine in the stool sample preparation solution is preferably within the range of 0.01 to $1.0 \times 10^{-3}$% by weight, more preferably within the range of 0.125 to $0.8 \times 10^{-3}$% by weight, and even more preferably within the range of 0.05 to $0.4 \times 10^{-3}$% by weight.

Furthermore, the suspending solution S and the stool sample processing solution P of the present invention are preferably acidic. This is to more effectively inhibit hydrolysis of nucleic acids. The pH of the stool sample preparation solution of the present invention is preferably within the range of 2 to 6.5, more preferably within the range of 3 to 6, and even more preferably within the range of 4.5 to 5.5.

In addition, the stool and the suspending solution S are preferably mixed rapidly. The components of the water-soluble organic solvent can be allowed to permeate rapidly by mixing and suspending the stool sample E in the suspending solution S followed by mixing with the water-soluble organic solvent. As a result, nucleic acid stabilization effects are rapidly obtained. Furthermore, in the case of suspending the stool sample E by mixing with the suspending solution S, or in the case of mixing the suspending solution S and the stool sample processing solution P, mixing may be carried out using a physical method. For example, mixing may carried out by vertically inverting the stool sample processing container or applying to a vortex or other type of shaking machine. In addition, mixing may also be carried out in the presence of mixing particles. There are no particular limitations on the type or material of the mixing particles, and may be particles composed of one type of material or particles composed of two or more types of materials. Examples of such mixing particles include particles made of glass, ceramics, plastic, latex or metal. In addition, the mixing particles may be magnetic particles or non-magnetic particles.

In the stool sample processing method of the present invention, in the case of using nucleic acids derived from a biological origin other than indigenous intestinal flora, namely nucleic acids contained in much smaller amounts than nucleic acids derived from indigenous intestinal flora contained in large amounts in stool samples, as the target nucleic acids of nucleic acid analysis in particular, the stool sample is preferably prepared using the stool sample preparation solution of the present invention. Nucleic acids present in stool are gradually lost due to decomposition and the like with the passage of time after voiding. Consequently, in the case the target nucleic acids are nucleic acids that are only present in small amounts in the stool sample, an amount of target nucleic acids sufficient for analysis cannot be recovered if analysis is carried out using a stool sample in which nucleic acid decomposition has progressed. In addition, even if the target nucleic acids were present in the stool sample immediately after voiding, there is the risk of the stool sample being determined to be negative (target nucleic acids are determined to not be present in the stool sample) if nucleic acid decomposition has progressed in the stool sample. Namely, since nucleic acids present in a stool sample can be stably preserved by preparing the stool sample using the stool sample preparation solution of the present invention, even if nucleic acids are present in only small amounts in the stool sample, an amount of nucleic acids sufficient for analysis can be efficiently recovered, thereby making it possible to improve the reliability of nucleic acid analysis.

Examples of nucleic acids derived from a biological origin other than indigenous intestinal flora as described above include nucleic acids derived from mammalian cells such as nucleic acids derived from cancer cells, and nucleic acids derived from causative microorganisms of infections present in the early or late stages of infections such as viral hepatitis. These nucleic acids may also be nucleic acids derived from parasites.

Furthermore, in the present invention, indigenous intestinal flora refers to bacterial cells present in comparatively large amounts in stool samples, and indicates indigenous flora that normally thrives in the intestines of animals such as humans. Examples of indigenous intestinal flora include obligatory anaerobic bacteria such as *Bacteroides* species, *Eubacterium* species, *Bifidobacterium* species or *Clostridium* species, and facultative anaerobic bacteria such as *Escherichia* species, *Enterobacter* species, *Klebsiella* species, *Citrobacter* species or *Enterococcus* species.

In addition, nucleic acid stabilization effects demonstrated by the water-soluble organic solvent component are not particularly affected by temperature conditions provided an adequate amount of water-soluble organic solvent is present. Thus, according to the stool sample processing method of the present invention, loss of nucleic acids present in a stool sample can be inhibited even in the case of having collected the stool sample at a temperature at which stool samples are normally collected, namely room temperature. In addition, a stool sample prepared according to the stool sample processing method of the present invention is able to stably preserve nucleic acids in the stool sample even in the case of storing or transporting at room temperature. However, stool samples are preferably stored at 50° C. or lower. The reason for this is that the concentration of the water-soluble organic solvent in the stool sample has the risk of falling below the concentration at which nucleic acid stabilization effects are adequately demonstrated due to volatilization and the like in cases of storing for long periods of time under high temperature conditions.

A stool sample prepared according to the stool sample processing method of the present invention is able to more stably preserve nucleic acids present in the stool sample, and particularly nucleic acids which are only present in comparatively small amounts in a stool sample derived from mammalian cells and the like due to a dehydrating action and protein denaturing action of a water-soluble organic solvent. Consequently, in the case of preparing a stool sample according to the stool sample processing method of the present invention, highly reliable analysis results can be expected to be obtained not only for stool samples immediately after preparation, but also in the case of analyzing nucleic acids using a stool sample following long-term storage or transport. In particular, nucleic acids present in a stool sample, and particularly nucleic acids derived from mammalian cells, can be stably stored at room temperature for a long period of time while minimizing time-based changes (changes occurring with the passage of time) with respect to molecular profiling of exfoliated colonocytes and other mammalian cells contained in stool samples. Consequently, by preparing a collected stool sample using the stool sample processing method of the present invention, stool samples can be stored or transported while inhibiting decomposition of nucleic acids, and particularly RNA that is susceptible to decomposition, even in cases which time has passed from stool sample collection to nucleic acid analysis or in cases in which the location where the stool sample was collected is located at a considerable distance form the location where nucleic acids are analyzed as is the case with routine health examinations and other forms of screening. In addition, since there is no need to provide special equipment for refrigeration or freezing or set special storage temperature conditions, stool samples can be stored or transported both easily and inexpensively.

The stool sample of the present invention can be used for various nucleic acid analyses in the same manner as other biological samples containing nucleic acids. In particular, it is preferably used for analysis of nucleic acids for investigating the onset of cancer or the occurrence of infections for which there is a strong need for early detection. In addition, it is also preferably used for nucleic acid analyses to investigate the onset of inflammatory diseases such as colitis, enteritis, gastritis or pancreatitis. It may also be used for testing for protruding lesions such as polyps as well as testing for various diseases of the large intestine, small intestine, stomach, liver, gallbladder and bile duct, such as gastric ulcer.

For example, the onset of colon cancer, pancreatic cancer or other cancers can be examined by detecting and analyzing nucleic acids derived from cancer cells, namely nucleic acids in which mutations and the like are occurring, from a stool sample. In addition, the onset of infection or the presence of parasites can be investigated by investigating whether or not nucleic acids derived from a pathogenic organism causing the infection, such as viral nucleic acids or parasite-derived nucleic acids, are detected from a stool sample. In particular, testing for infections can be carried out both non-invasively and easily by using a stool sample to detect pathogenic organisms excreted into the stool, such as hepatitis A virus or hepatitis E virus. In addition, the onset of a bacterial infection can be investigated by investigating whether or not nucleic acids derived from pathogenic bacteria other than indigenous intestinal flora, such as bacteria causing food poisoning or pathogenic microorganisms such as enterohemorrhagic *Escherichia coli* O-157, are detected.

In particular, a marker indicating a neoplastic transformation or a marker indicating an inflammatory gastrointestinal disease is preferably detected by nucleic acid analysis. Examples of markers indicating neoplastic transformation include known cancer markers such as carcinoembryonic antigen (CEA) or sialyl Tn antigen (STN), and mutations such as those of APC gene, p53 gene or K-ras gene. In addition, detection of methylation of genes such as p16, hMLH1, MGMT, p14, APC, E-cadherin, ESR1 or SFRP2 is also useful as a diagnostic marker of colon diseases (see, for example, Lind, et al., "A CpG island hypermethylation profile of primary colorectal carcinomas and colon cancer cell lines", Molecular Cancer, 2004, Vol. 3, Chapter 28). In addition, DNA derived from *Helicobacter pylori* present in a stool sample has been previously reported to be used as a stomach cancer marker (see, for example, Nilsson, et al., Journal of Clinical Microbiology, 2004, Vol. 42, No. 8, pp. 3781-8). On the other hand, an example of a marker that indicates an inflammatory gastrointestinal disease is nucleic acid derived from Cox-2 gene.

Nucleic acids can be recovered extremely efficiently from a stool sample prepared according to the stool sample processing method of the present invention. Accordingly, this stool sample can be used extremely preferably for analysis of not only nucleic acids derived from indigenous intestinal flora present in large amounts in stool, but also nucleic acids derived from mammalian cells present in trace amounts. In particular, since the sample is a stool sample, nucleic acids derived from gastrointestinal cells of the large intestine, small intestine, stomach and the like are analyzed preferably, and nucleic acids derived from exfoliated colonocytes are analyzed particularly preferably.

A diverse range of substances are present in stool samples, and there are also numerous substances present that can inhibit nucleic acid analysis. Consequently, analysis accuracy can be further improved by recovering nucleic acids from a stool sample and using the recovered nucleic acids. There are no particular limitations on the method used to recover nucleic acids from stool samples, and any method can be used provided it is a method that is ordinarily used in the case of recovering nucleic acids from a sample. The stool sample of the present invention mainly contains nucleic acids of a biological origin other than indigenous intestinal flora such as mammalian cells (also simply referred to as mammalian cells), and nucleic acids derived from indigenous intestinal flora. When recovering nucleic acids from a stool sample, although nucleic acids derived from mammalian cells and nucleic acids derived from indigenous intestinal flora may be recovered separately, they are particularly preferably recovered simultaneously. By recovering nucleic acids derived from mammalian cells and nucleic acids derived from indigenous intestinal flora simultaneously, nucleic acids derived from mammalian cells present in extremely small number can be recovered more efficiently than in the case of recovering nucleic acids after having isolated the mammalian cells from stool as a result of the nucleic acids derived from indigenous intestinal flora present in large amounts in stool functioning as carriers. Furthermore, the nucleic acids recovered from a stool sample may be DNA, RNA or both DNA and RNA.

A stool sample obtained by the processing described above can be processed in various ways in accordance with a specific application using known techniques. For example, proteins in the stool sample can be denatured by adding a compound that is ordinarily used as a protein denaturing agent, such as a chaotropic salt, organic solvent or surfactant, to the stool sample. The same chaotropic salts and surfactants as those listed as examples of chaotropic salts and surfactants able to be added to the stool sample preparation solution of the present invention can be used, and phenol is preferably used as an organic solvent. The phenol may be neutral or acidic. In the case of using an acidic phenol, RNA can be more selectively extracted into an aqueous layer than DNA. Furthermore, in the case of adding a chaotropic salt, organic solvent or surfactant to a stool sample, one type of compound may be added or two or more types of compounds may be added.

Here, in the case of removing a stool sample from the stool sample processing container 1, large fibrous substances and the like may be removed from a stool sample by removing the stool collection tool 100 and replacing with a cover provided with a filter. In addition, the stool sample may also be filtered by preliminarily installing a filter in the lower portion of the processing solution holding container 121 and peeling off the sealing material when using a sealing material for the cover.

In addition, after having denatured protein as described above, the denatured protein may be removed before recovering nucleic acids. Removing preliminarily denatured protein prior to recovering nucleic acids makes it possible to improve the quality of the recovered nucleic acids. Denatured protein can be removed by a known method. For example, denatured protein can be removed by precipitating denatured protein by centrifugation and then recovering only the supernatant. In addition, denatured protein can be removed more completely than in the case of simply centrifuging by first adding chloroform followed by centrifuging after adequately stirring and mixing with a vortex to precipitate the denatured protein and then recovering only the supernatant.

Recovery of nucleic acids following protein denaturation can be carried out by a known method such as ethanol precipitation or cesium chloride ultracentrifugation. In addition, nucleic acids can also be recovered by adsorbing nucleic acids that eluted during protein denaturation onto an inorganic support and then eluting the adsorbed nucleic acids from the inorganic support. A known inorganic support capable of adsorbing nucleic acids can be used for the inorganic support that adsorbs nucleic acids. In addition, there are no particular limitations on the form of the inorganic support, and may be a particulate or film-like inorganic support. Examples of inorganic supports include silica-containing particles (beads) such as silica gel, siliceous oxides, glass or diatomaceous earth, and porous films such as those made of Nylon, polycarbonate, polyacrylate or nitrocellulose. A solvent that is ordinarily used to elute nucleic acids from these known inorganic supports can be suitably used for the solvent that elutes the adsorbed nucleic acids from the inorganic support in consideration of the types of nucleic acids recovered, the subsequent nucleic acid analysis method and the like. Purified water is used particularly preferably for the elution solvent. Furthermore, after having adsorbed nucleic acids onto the inorganic support, the inorganic support onto which nucleic acids have adsorbed is preferably washed with a suitable washing buffer.

Furthermore, in the case of preparing a stool sample using a stool sample preparation solution containing an adequate concentration of chaotropic salt or surfactant for eluting nucleic acids from mammalian cells, protein denaturation treatment can be omitted when recovering nucleic acids from the stool sample.

In the case of preparing a stool sample using a stool sample preparation solution not containing an adequate concentration of chaotropic salt or surfactant for eluting nucleic acids from mammalian cells, it is preferable to recover solid components from the stool sample prior to protein denaturation treatment. The ratio of liquid component to solid component in the stool sample is preferably large in order to rapidly mix the stool sample E and the stool sample preparation solution. Therefore, the burden on the tester during nucleic acid recovery and analysis and the scale required for equipment and the like can be reduced by removing the stool sample preparation solution from the stool sample and only recovering the solid portion containing mammalian cells and indigenous intestinal flora. In addition, the effect of the water-soluble organic solvent on the step for recovering nucleic acids from the solid component can be reduced by removing the water-soluble organic solvent from the solid component. For example, only the solid component can be recovered by centrifuging the stool sample to precipitate the solid component and then removing the supernatant. In addition, only the solid component can also be recovered by filtration and the like. Moreover, the recovered solid component is preferably washed using a suitable buffer such as PBS (phosphate-buffered saline, pH 7.4).

Furthermore, although a protein denaturing agent such as a chaotropic salt may be added directly to the recovered solid component, the protein denaturing agent is preferably added after first suspending in a suitable elution reagent. In the case of recovering DNA, a phosphate buffer or Tris buffer, for example, can be used for the elution reagent. A reagent in which DNase has been deactivated by high-pressure steam sterilization and the like is preferable, and a reagent containing a protease such as protease K is more preferable. On the other hand, in the case of recovering RNA, although a citrate buffer, for example, can be used for the elution reagent, since RNA is extremely susceptible to decomposition, it is preferable to use a buffer that contains an RNase inhibitor such as guanidine thiocyanate or guanidine hydrochloride.

Nucleic acids need not be recovered from the stool sample depending on the subsequent analysis method. More specifically, nucleic acids can be used directly for nucleic acid analysis after having been eluted from mammalian cells or indigenous intestinal flora present in the stool sample. For example, in cases in which a large amount of pathogen and the like is present in the stool sample and those pathogen-derived nucleic acids are to be analyzed, after recovering only the solid component from the stool sample, an elution reagent such as PBS containing a protease such as protease K is added to and mixed with the solid component. Genes and the like derived from the pathogen can then be detected by using the resulting homogeneous stool sample solution directly for nucleic acid analysis. In addition, recovery of nucleic acids from a stool sample may also be carried out using a commercially available kit such as a nucleic acid extraction kit or virus detection kit.

Nucleic acids recovered from a stool sample can be analyzed using a known nucleic acid analysis method. Examples of nucleic acid analysis methods include methods involving quantification of nucleic acids and methods involving detection of specific base sequence regions using PCR and the like. In addition, in the case of recovering RNA, analysis can be carried out in the same manner as DNA by synthesizing cDNA by a reverse transcription reaction (RT-PCR: reverse transcription-polymerase chain reaction) and then using that cDNA. For example, the onset of cancer can be investigated by detecting a base sequence region encoded by a cancer gene or by detecting the presence of a genetic mutation such as base sequence region containing a microsatellite. In the case of using DNA recovered from a stool sample, methylation of the DNA or mutations such as base insertions, deletions, substitutions, duplications or inversions can be detected. In addition, in the case of using recovered RNA, mutations such as base insertions, deletions, substitutions, duplications, inversions or splicing hybrids (isoform) can be detected in the RNA. In addition, the amount of RNA expressed can also be detected. mRNA expression analyses, K-ras gene mutation analyses and DNA methylation analyses are carried out particularly preferably. Furthermore, these analyses can be carried out according to known methods in this field. In addition, a commercially available kit such as a K-ras gene mutation analysis kit or methylation detection kit may also be used.

Figure 3:
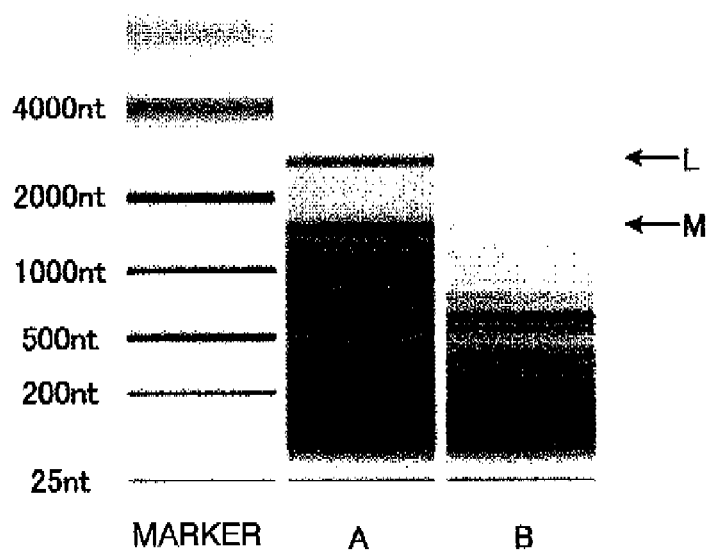
FIG. 3 is a drawing that confirms RNA (A), recovered by using a suspending solution, and RNA (B), recovered without using a suspending solution, by electrophoresis.

FIG. 3 shows electrophoresis images comparing RNA recovered from a stool sample in which the stool sample E was processed using the suspending solution S, and RNA recovered from a stool sample in which the stool sample E was processed without using the suspending solution S.

Sample A was obtained by mixing stool with 4 ml of PBS, suspending by shaking for 10 seconds, adding 6 ml of 100% ethanol, shaking for 10 seconds and extracting RNA according to a known technique. Sample B was obtained by adding 70% ethanol to stool, shaking for 20 seconds, and extracting RNA according to a known technique. The stool samples used for both samples consisted of 1 g each collected from the same stool with a stool collection tool within 1 hour after stool collection. In addition, the final ethanol concentrations of the prepared samples A and B were equal.

The samples A and B prepared according to the stool processing method described above were allowed to stand for 24 hours at room temperature followed by extraction of RNA. RNA recovery was specifically carried out in the manner described below. First, tubes containing samples A and B were centrifuged, the supernatant was removed from each, and 3 mL of a phenol mixture (Isogen, Nippon Gene) were added to the resulting solid component followed by adequately mixing with a homogenizer for 30 seconds or more. Subsequently, 3 mL of chloroform were added to each tube of samples A and B, and after adequately mixing using a vortex, the tubes were centrifuged for 20 minutes at 12,000×g and 4° C. The supernatant (aqueous layer) obtained by centrifuging each tube of samples A and B was passed over an RNA recover column provided in a RNeasy Midi Kit (Qiagen), and RNA derived from samples A and B was recovered by washing the RNA recovery column and eluting RNA in accordance with the protocol provided with the kit.

Subsequently, the RNA recovered from samples A and B was electrophoresed with an RNA 6000 Nano Assay Kit (Agilent), and RNA recovered from samples A and B was detected with an Agilent 2100 Bioanalyzer (Agilent) (refer to the manual provided with the kit for information on the procedure). Standard samples exhibiting a number of nucleotides from 25 nt to 4000 nt were used for the markers in FIG. 3, and the markers were used based on the constituent units of DNA or RNA that composed the samples.

The results of comparing the band patterns of samples A and B in FIG. 3 are described below. In the band pattern of sample A, dark bands were respectively confirmed in the vicinity of 3000 nt as indicated by arrow L and in the vicinity 1500 nt as indicated by arrow M. In the band pattern of sample B, bands were observed in the vicinity of arrows L and M to a degree that they were just able to be confirmed. Since band darkness is proportional to concentration in this method, the concentrations of RNA in sample A in the vicinity of arrows L and M (namely, the amount of RNA recovered from sample A) are shown to greatly exceed the concentrations of RNA of sample B (namely, the amount of RNA recovered from sample B). Here, arrow L indicates a 23 S band of high-quality bacterial RNA, while arrow M indicates a 16S band. Improving the amounts of these 23S and 16S RNA recovered leads to improvement of analysis accuracy. In addition, the amount of RNA recovered from sample B at 25 to 500 nt is greater overall than sample A. This indicates that RNA inherently expressed in the vicinity of arrows L and M had been decomposed. This result indicates that non-decomposed RNA can be recovered with high accuracy by processing the stool sample with suspending solution S prior to processing the stool sample with stool sample processing solution.

Here, setting of temperature conditions is an important aspect in conventional stool sample processing methods such as recovering nucleic acids by maintaining a low temperature, while in the case of methods consisting of the addition of a bactericide and the like, there was the problem of the procedure for separating exfoliated colonocytes from the stool sample being excessively complex. In addition, methods using a storage solution are only effective for nearly isolated cells, and the direct use of a biological sample containing a diverse range of substances in the manner of stool samples not only made processing difficult, but also resulted in low recovery efficiency. Although conventional stool sample processing containers allow the stool sample to be suspended in the container, since it is necessary to add a processing solution and the like to the suspending solution S, there was the problem of a decrease in nucleic acid recovery efficiency.

In contrast, the stool sample processing method and stool sample processing container related to the first embodiment makes it possible to prepare a stool sample from an easily collected stool and recover nucleic acids with high accuracy by collecting the stool in a stool collection container in which the stool sample processing solution of the present invention has been housed in advance. In addition, processing can be carried out at normal temperatures, and after suspending the stool by using a suspending solution, nucleic acids in the sample are stabilized by a stool sample processing solution, thereby enabling various processing to be subsequently carried out. In addition, since the processing container of the present invention is easy to operate (easy to use), it can even be used at home. Moreover, since the suspending solution and the stool sample processing solution are housed separately in the processing container of the present invention, each solution can be housed selectively, which is useful in terms of carrying out various processing.

Second Embodiment

Figure 4:
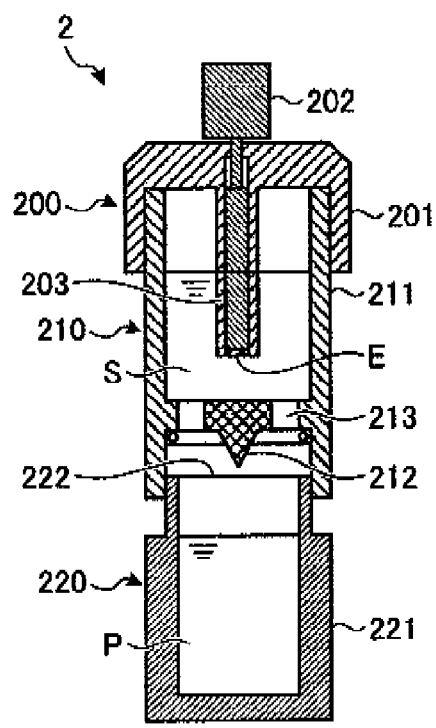
FIG. 4 is a schematic drawing showing a stool sample processing container 2 relating to a second embodiment.

FIG. 4 is a schematic drawing showing the general configuration of a stool sample processing container 2 relating to a second embodiment of the present invention. This stool sample processing container 2 is provided with a stool collection tool 200, a suspending solution holding portion 210 and a processing solution holding portion 220, each is present in the stool sample processing container in a sealed state, and each is removable. In addition, the suspending solution S and the stool sample processing solution P that compose a stool sample preparation solution are respectively housed in a suspending solution holding container 211 and a processing solution holding container 221.

In FIG. 4, a stool sample is collected by a stool collection rod 203 of the stool collection tool 200. A piston 202 is incorporated within the stool collection rod, and the amount of stool collected can be made to be constant (adjusted) by adjusting this piston 202. After having collected a stool sample with the stool collection rod 203, a cover 201 is attached to the suspending solution holding container 211, and by pressing the piston 202, the stool sample E is pushed out and mixed with the suspending solution S to obtain a stool suspension. Furthermore, in the present embodiment, the cover 201, the stool collection rod 203 and the piston 202, which introduce the stool sample E into the suspending solution holding container 221, are collectively referred to as an introduction mechanism. Subsequently, when the suspending solution holding container 211 is pressed into the processing solution holding container 221, a protrusion of a protruding portion 212 punctures a sealing film 222 that seals the processing solution holding container 221 causing the sealing film 222 to rupture and resulting in the stool suspension mixing with the stool sample processing solution P. Furthermore, in the present embodiment, the protruding portion 212 and the sealing film 222 are referred to as a release mechanism. The stool sample processing solution P and the stool suspension are able to flow through a communicating hole 213 around the protruding portion 212, and can be easily mixed by vertically inverting the stool sample processing container 2. Similar to the first embodiment, a mechanism for removing the stool sample may consist of replacing the cover 201 with a cover provided with a filter then filtering the stool sample, or a filter may be formed in the lower portion of the processing liquid storage container 221.

Figure 5:
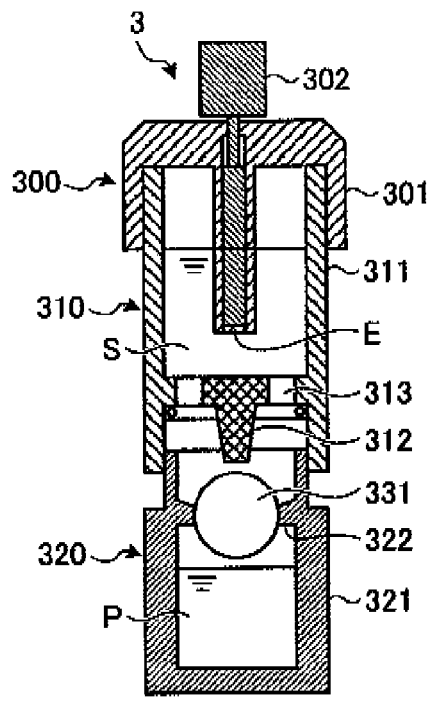
FIG. 5 is a schematic drawing showing a stool sample processing container 3, which is a first variation of a stool sample processing container 2 relating to a second embodiment.

Here, an explanation is provided of a stool sample processing container 3, which is a first variation of the stool sample processing container 2 shown in FIG. 4, with reference to FIG. 5. The stool sample processing container 3 is composed of a stool collection tool 300, a suspending solution holding portion 310 and a processing solution holding portion 320 in the same manner as the stool sample processing container 2. Moreover, a piston 302 is installed in the stool collection tool 300, and the suspending solution S is housed in a suspending solution holding container 311 while the stool sample processing solution P is housed in a processing solution holding container 321. Furthermore, in the present embodiment, members comprising a cover 301, the stool collection tool 300 and the piston 302, which introduce the stool sample E into the suspending solution holding container 311, are referred to as an introduction mechanism. In the stool sample processing container 3, a spherical sealant 331 is held in a sealant shaft portion 322 to prevent the stool sample processing solution P from flowing into the suspending solution S. As a result of a protruding portion 312 pushing the spherical sealant 331 into the processing solution holding container 321, the stool suspension and the stool sample processing solution P are mixed by mutually flowing through a communicating hole 313. Furthermore, in the present embodiment, members including the sealant 331, the sealant shaft portion 322 and the protruding portion 312 are referred to as a release mechanism.

Figure 6:
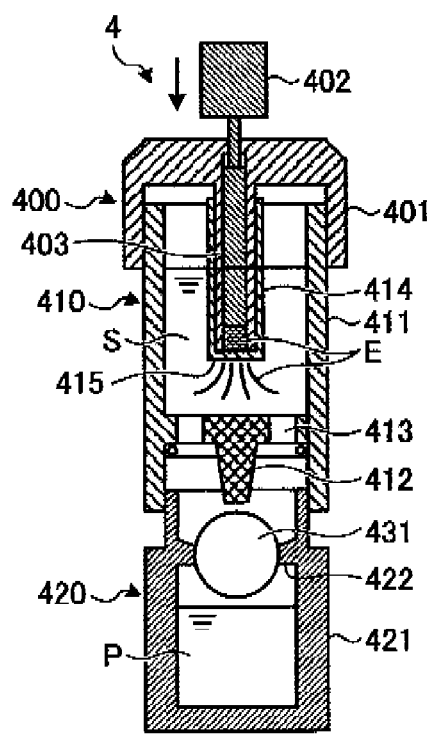
FIG. 6 is a schematic drawing showing a stool sample processing container 4, which is second variation of a stool sample processing container 2 relating to a second embodiment.

In addition, an explanation is further provided of a stool sample processing container 4, which a second variation of the stool sample processing container 2, with reference to FIG. 6. The stool sample processing container 4 shown in FIG. 6 is provided with a stool collection tool 400, a suspending solution holding portion 410 and a processing solution holding portion 420, and the suspending solution S is housed in a suspending solution holding container 411, while the stool sample processing solution P is housed in a processing solution holding container 421. Moreover, the suspending solution holding portion 410 is provided with a slider 414 that scrapes off excess stool adhered to a protruding portion 412 and a stool collection rod 403, and a sample cutting portion 415, having a mesh-like filter, is formed in the lower portion of the slider 414. The stool sample E, which has been pushed out from the piston 402 by the sample cutting portion 415, is ejected into the suspending solution S in the form of a thread. Accordingly, even stool samples of high viscosity can be suspended easily. Furthermore, in the present embodiment, members including a cover 401, the stool collection rod 403, the slider 414, the piston 402 and the sample cutting portion 415, which introduce the stool sample E into the suspending solution holding container 411, are referred to as an introduction mechanism.

Subsequently, the stool suspension, which is obtained as a result of the protruding portion 412 releasing a sealant 431 held in a sealant shaft portion 422 into the processing solution holding container 421, is mixed with the stool sample processing solution P by mutually flowing through a communicating hole 413. Furthermore, in the present embodiment, members including the sealant 431, the sealant shaft portion 422 and the protruding portion 412 are referred to as a release mechanism.

In this second embodiment, changes in the amount of stool collected can be accommodated by using the pistons 202, 302 and 402. In addition, as a result of the stool sample E being cut into the form of a thread by the sample cutting portion 415 after being pushed out by the piston 402, even highly viscous stool samples can be finely dispersed by suspending, thereby making it possible to recover nucleic acids with high accuracy.

Third Embodiment

Figure 7:
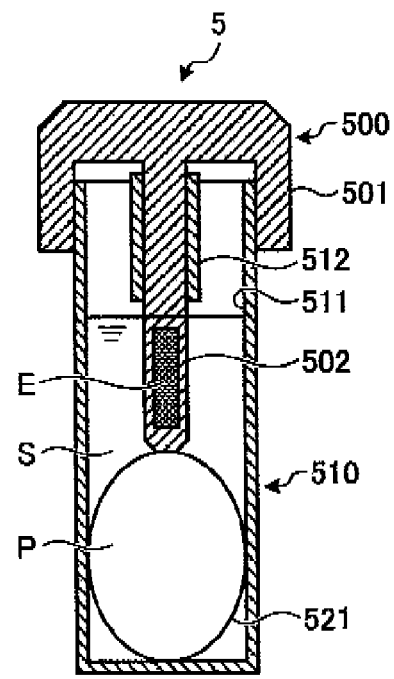
FIG. 7 is a schematic drawing showing a stool sample processing container 5 relating to a third embodiment.

FIG. 7 is a schematic drawing showing the general configuration of a stool sample processing container 5 relating to a third embodiment of the present invention. The stool sample processing container 5 shown in FIG. 7 is provided with a stool collection tool 500, a suspending solution holding portion 510 and a processing solution holding container 521, and each is present within the stool sample processing container 5 in a sealed state. In addition, the suspending solution S and the stool sample processing solution P that compose a stool sample preparation solution are respectively housed in a suspending solution holding container 511 and the processing solution holding container 521.

In the stool sample processing container 5, the processing solution holding container 521 is housed within the suspending solution holding container 511. The suspending solution holding container 511 and the processing solution holding container 521 are formed from an elastic material, and the tensile strength of the processing solution holding container 521 is lower than that of the suspending solution holding container 511. Simultaneous to sampling the stool sample E with a stool collection rod 502 and attaching the suspending solution holding container 511 and a cover 501, excess stool adhered to the stool collection rod 502 is scraped off by a slider 512. Subsequently, the suspending solution S and the stool sample E to suspend the stool sample E therein, and the resulting stool suspension is mixed with the stool sample processing solution P.

Figure 8:
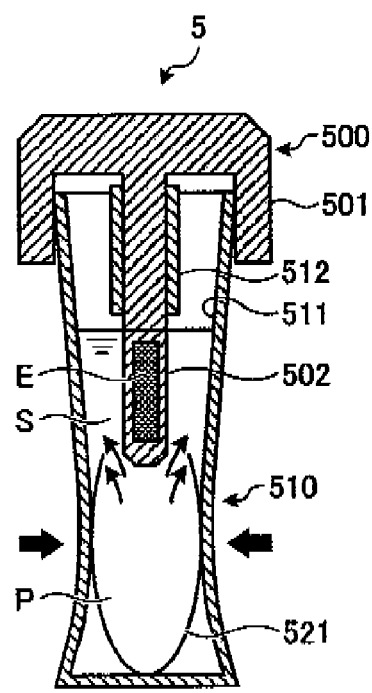
FIG. 8 is a schematic drawing showing a stool sample processing container 5 relating to a third embodiment.

As shown in FIG. 8, the method for mixing the stool sample processing solution P consists of pressing on the suspending solution holding container 511 in the vicinity of the processing solution holding container 521 to increase the internal pressure of the processing solution holding container 521, and thereby rupturing the processing solution holding container 521 to release the stool sample processing solution P there within into the stool suspension.

Furthermore, only the processing solution holding container 521 is ruptured by pressing as a result of providing a difference in tensile strength between the suspending solution holding container 511 and the processing solution holding container 521. The stool sample obtained by this mixing is used to recover nucleic acids.

Furthermore, the processing solution holding container 521 is preferably formed using a soft resin such as silicone rubber. In addition, the suspending solution holding container 511 may be made to be resistant to deformation caused by pressing by forming the coupling with the cover 501 from a hard resin to maintain a seal. In addition, the processing solution holding container 521 may be ruptured by forming the end of the stool collection rod 502 to a point.

Figure 9:
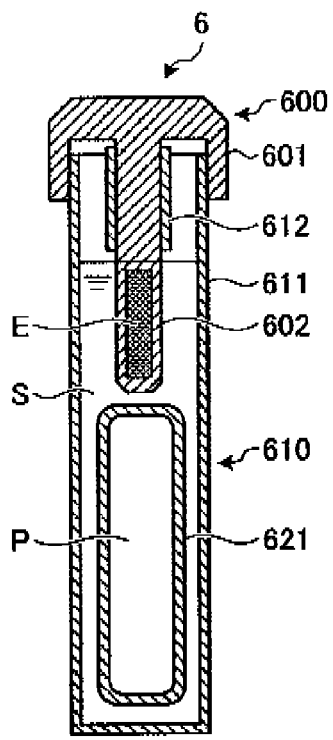
FIG. 9 is a schematic drawing showing a stool sample processing container 6, which a variation of a stool sample processing container 5 relating to a third embodiment.
Figure 10:
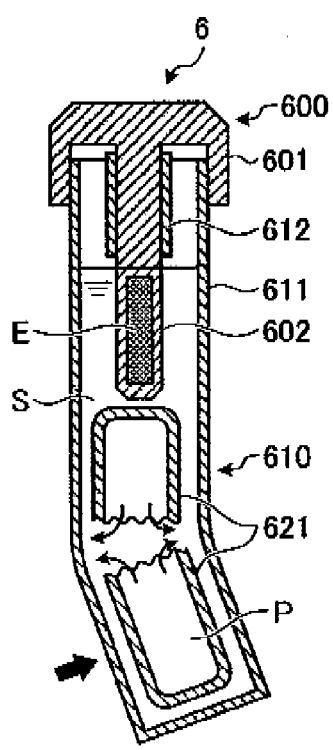
FIG. 10 is a schematic drawing showing a stool sample processing container 6, which is a variation of a stool sample processing container 5 relating to a third embodiment.

In addition, the following provides an explanation of a stool sample processing container 6 that is a variation of the stool sample processing container 5 with reference to FIG. 9. The stool sample processing container 6 shown in FIG. 9 is provided with a stool collection tool 600, a suspending solution holding portion 610 and a processing solution holding container 621, and a stool collection rod 602 is formed in the stool collection tool 600, while a slider 612 is formed in the suspending solution holding portion 610. In addition, a suspending solution holding container 611 and the processing solution holding container 621 are formed from an elastic material and the like. Consequently, by providing a portion having a lower tensile strength than the suspending solution holding portion 611 in a portion of the processing solution holding container 621, and bending the suspending solution holding container 611 and the processing solution holding container 621, the portion of low tensile strength of the processing solution holding container 621 is ruptured. Furthermore, in order to allow the processing solution holding container 621 to be ruptured with little effort, the container may be formed from a hard resin such as plastic and perforations may be formed in a portion of the container so facilitate rupturing. In addition, the coupling between the suspending solution holding container 611 and a cover 601 may be formed with a hard resin to maintain sealing of the container in the same manner as the stool sample processing container 5.

Since the stool sample processing containers 5 and 6 relating to the third embodiment only involve handling of the stool collection tools 500 and 600 and the suspending solution holding containers 511 and 611, they have a simpler structure than the stool sample processing containers 1 to 4. In addition, when comparing the methods used to mix the separated stool suspension and stool sample processing solution P, since the stool sample processing solution P is released into the stool suspension, the amount of time required to mix the stool suspension and the stool sample processing solution P can be shortened. Furthermore, in the present embodiment, those members comprising the covers 501 and 601, the stool collection rods 502 and 602, and the sliders 512 and 612, which introduce the stool sample E into the suspending solution holding container 511, are referred to as an introduction mechanism, while those members including the processing solution holding containers 521 and 621 are referred to as a release mechanism.

Fourth Embodiment

Figure 11:
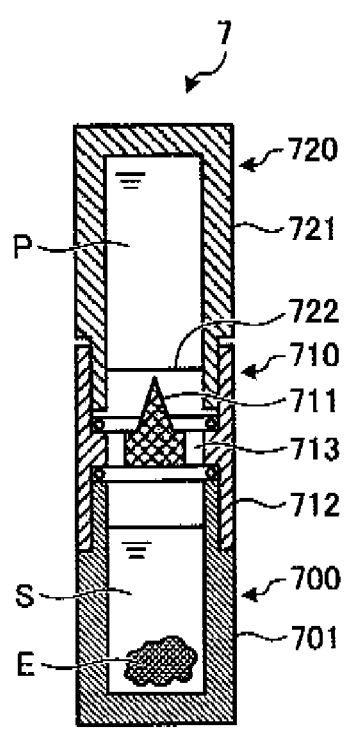
FIG. 11 is a schematic drawing showing a stool sample processing container 7 relating to a fourth embodiment.

FIG. 11 is a schematic drawing showing the general configuration of a stool sample processing container 7 relating to a fourth embodiment of the present invention. This stool sample processing container 7 is provided with a suspending solution holding portion 700, a coupling portion 710 and a processing solution holding portion 720, and each is present within the stool sample processing container 7 in a sealed state. In addition, the suspending solution S and the stool sample processing solution P that compose a stool sample preparation solution are respectively housed in a suspending solution holding container 701 and a processing solution holding container 721.

First, a sampled stool sample E is introduced into the suspending solution holding container 701 preliminarily housing the suspending solution S, and the suspending solution holding container 701, a joining portion 712 and the processing solution holding container 721 are respectively connected. Furthermore, a slight gap is maintained between the processing solution holding portion 720 and the coupling portion 710 so that the stool sample processing solution P is not released until the stool sample E is suspended in the suspending solution S. Once the stool sample E is suspended in the suspending solution S to obtain a stool suspension, a protrusion of a protruding portion 711 punctures a sealing film 722 as a result of pressing down on the processing solution holding container 721, thereby rupturing the sealing film 722. As a result, the stool sample processing solution P and the stool suspension flow through a communicating hole 713 and mix. A stool sample is then prepared according to the aforementioned processing.

Furthermore, although the present embodiment does not contain an explanation of members equivalent to an introduction mechanism, the stool sample E may be introduced into the suspending solution holding container 701 using a conventional method or using an introduction mechanism described in the aforementioned embodiments. In addition, in the present embodiment, those members including the protruding portion 711 and the sealing film 722 are referred to as a release mechanism.

Since each component of stool sample processing container 7 relating to the fourth embodiment is provided separately, the number of choices available during operation increase. For example, by installing a sealing film in the suspending solution holding container 701 as well to seal the suspending solution S, and releasing the contents of the suspending solution holding container 701 with the protruding portion 711 of the coupling portion 710 at the time of use, solution stability can be expected to be improved by, for example, preventing oxidation of the suspending solution S. Subsequently, sample preparation and processing as described above can also be carried out by inverting the coupling portion 710. In addition, by using a spherical sealant like that described in the second embodiment, the sealant that is released into the suspending solution S and the stool sample processing solution P acts in the manner of stirring beads and the like, and can be expected to demonstrate the effect of promoting mixing of each solution.

Furthermore, the present invention is not limited to the first to fourth embodiments described above, but rather includes various other embodiments not described herein, and can undergo various modifications in design and the like within a range that does not deviate form the technical scope specified in the claims.

INDUSTRIAL APPLICABILITY

According to the stool sample processing method and stool sample processing container of the present invention, by collecting stool in a stool sample container preliminarily housing the stool sample preparation solution of the present invention, a stool sample can be easily prepared from the collected stool and nucleic acids can be recovered and processed with high accuracy and in a stable state. In addition, since the processing container of the present invention is easy to operate (easy to use), it can also be used at home. Moreover, since a suspending solution and a stool sample processing solution are housed separately in the processing container of the present invention, each solution can be housed selectively, which is useful in terms of carrying out various processing.

BRIEF DESCRIPTION OF THE REFERENCE SYMBOLS

1-7, Stool sample processing container
100, 200, 300, 400, 500, 600, 700 Stool collection tool
101, 201, 301, 401, 501, 601, 701 Cover
102, 203, 403, 502, 602 Stool collection rod
110, 210, 310, 410, 510, 610, 700 Suspending solution holding portion
111, 211, 311, 411, 511, 611, 701 Suspending solution holding container
112, 414, 512, 612 Slider
120, 220, 320, 420, 720 Processing solution holding portion
121, 221, 321, 421, 521, 621, 721 Processing solution holding container
122, 322 Sealant shaft portion
131, 331, 431 Sealant
202, 302, 402 Piston
212, 312, 412, 711 Protruding portion
213, 313, 413, 713 Communicating hole
222, 722 Sealing film
415 Sample cutting portion
710 Coupling portion
712 Joining portion
E Stool sample
P Stool sample processing solution
S Suspending solution

The invention claimed is:

1. A stool sample processing method for preparing and processing a stool sample for recovering a nucleic acid from the collected stool sample, comprising:
   forming a stool suspension in which the collected stool sample is suspended with a suspending solution, and
   preparing the stool sample by mixing the stool suspension with a stool sample processing solution that stabilizes the nucleic acid, the stool sample processing solution being acidic;
   wherein the suspending solution and the stool sample processing solution are initially separated in a container,
   wherein the stool sample processing solution is mixed with the collected stool sample and the stool sample suspending solution by application of a force on the container,
   wherein the stool sample is collected by a collection tool, and
   wherein the preparing step is performed by connecting the collection tool to the container.

2. The stool sample processing method according to claim 1, wherein the suspending solution is selected from the group consisting of water, physiological saline or a buffer.

3. The stool sample processing method according to claim 1, wherein the stool sample processing solution is a water-soluble organic solvent.

4. The stool sample processing method according to claim 3, wherein the water-soluble organic solvent is a water-soluble alcohol and/or ketone.

5. The stool sample processing method according to claim 3, wherein the stool sample contains 30% or more of the water-soluble organic solvent.

6. The stool sample processing method according to claim 4, wherein the water-soluble alcohol is one or more types selected from the group consisting of ethanol, propanol and methanol.

7. The stool sample processing method according to claim 4, wherein the ketone is acetone and/or methyl ethyl ketone.

8. The stool sample processing method according to claim 3, wherein the water-soluble organic solvent is an aldehyde.

9. The stool sample processing method according to claim 3, wherein the stool sample contains 0.01 to 30% of the water-soluble organic solvent.

10. The stool sample processing method according to claim 3, wherein the water-soluble organic solvent contains an organic acid.

11. The stool sample processing method according to claim 3, wherein the water-soluble organic solvent contains a chelating agent and/or polycation.

12. The stool sample processing method according to claim 1, wherein the stool sample processing solution has a pH in the range of 2 to 6.5.

13. The stool sample processing method according to claim 1, wherein the stool sample processing solution has a pH in the range of 3 to 6.

14. The stool sample processing method according to claim 1, wherein the stool sample processing solution has a pH in the range of 4.5 to 5.5.

* * * * *